United States Patent [19]

Hulon

[11] Patent Number: 5,297,561
[45] Date of Patent: Mar. 29, 1994

[54] BLOOD COLLECTION TUBE ASSEMBLY

[76] Inventor: Walter C. Hulon, P.O. Box 40745, Baton Rouge, La. 70835

[21] Appl. No.: 555,573

[22] Filed: Jul. 19, 1990

Related U.S. Application Data

[63] Continuation-in-part of Ser. No. 366,468, Jun. 15, 1989, abandoned.

[51] Int. Cl.⁵ .................................................. A61B 5/00
[52] U.S. Cl. .................................... 128/764; 604/403; 604/415; 215/31; 215/33; 215/355; 215/DIG. 3
[58] Field of Search ................... 604/82, 84, 86, 403, 604/415–416, 232, 234, 241; 128/763–764, 765, 770; 206/828; 215/31, 33, 247, 295–296, 300, 355, DIG. 3; 220/306–307, 352, 354, 356, DIG. 19

[56] References Cited

U.S. PATENT DOCUMENTS

| | | | |
|---|---|---|---|
| 3,433,216 | 3/1969 | Mattson | 128/765 X |
| 3,776,218 | 12/1973 | Svensson | 128/765 |
| 4,166,450 | 9/1979 | Abramson | 128/764 |
| 4,181,233 | 1/1980 | Gouveia | 215/247 |
| 4,216,782 | 8/1980 | Sarstedt | 128/764 |
| 4,227,620 | 10/1980 | Conway | 215/355 |
| 4,320,770 | 3/1982 | Etherington et al. | 128/766 |
| 4,333,478 | 6/1982 | Krieg | 128/764 |
| 4,843,017 | 6/1989 | Oberhardt et al. | 436/177 |
| 4,856,533 | 8/1989 | Anraku et al. | 128/763 |
| 4,863,453 | 9/1989 | Berger et al. | 604/415 |
| 4,893,636 | 1/1990 | Cook et al. | 128/764 |
| 4,907,600 | 3/1990 | Spencer | 604/240 X |
| 4,915,243 | 4/1990 | Tatsumi et al. | 215/247 |
| 4,967,763 | 11/1990 | Nugent et al. | 128/763 |

FOREIGN PATENT DOCUMENTS 1025894 4/1953 France .................... 220/DIG. 19

OTHER PUBLICATIONS

Becton Dickinson, "Vacutainer Brand SST Tubes for Serum Separation", 1987.
Becton Dickinson, "Vacutainer Brand PST Tube for Plasma Separation", 1986.
Doctors Office Product Review, "Plastic Encased Tubes", date unknown.

*Primary Examiner*—C. Fred Rosenbaum
*Assistant Examiner*—Corrine Maglione
*Attorney, Agent, or Firm*—Harrison & Egbert

[57] ABSTRACT

An air-evacuated blood collection tube assembly comprising an air-evacuated tubular container having an open end and a closed end, and a cannula-penetrable self-sealing gas-proof closure in sealing engagement with the open end of the container so as to maintain the vacuum inside the container. The closure has an end interior of the container and an end exterior of the container. The end interior has a first notch formed adjacent to the container wall. The end exterior includes a first notch that is aligned with the notch on the end interior of the container. The tubular container is formed of a polyethylene terephthalate material. The open end of the tubular container is flared outwardly. A hump extends inwardly of the inner diameter of the tubular container. The closure has an indented ring that is formed so as to receive this hump during engagement with the tubular container.

10 Claims, 5 Drawing Sheets

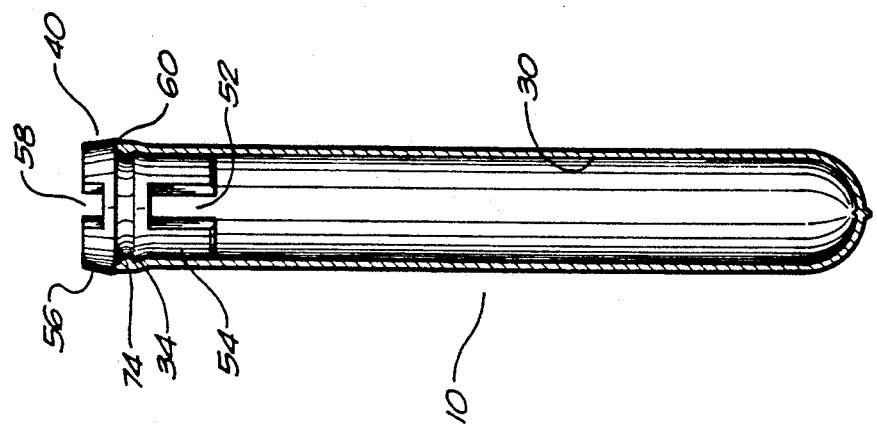
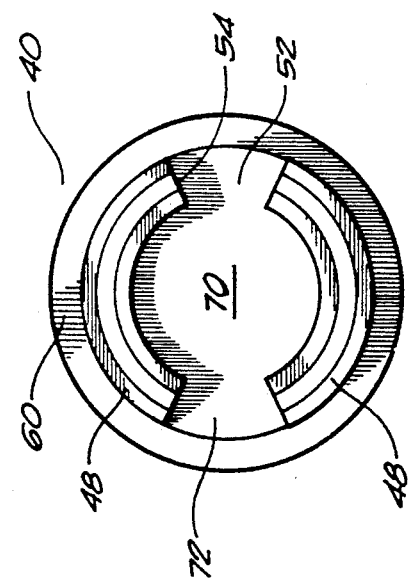

BLOOD COLLECTION TUBE ASSEMBLY

RELATED APPLICATION

The present application is a continuation in part of U.S. patent application Ser. No. 07/366,468, filed on Jun. 15, 1989, and entitled "Improved Blood Collection Tube", now abandoned.

TECHNICAL FIELD

The present invention relates to blood collection tubes. More particularly, the present invention relates to plastic blood collection tubes, closures, and systems used for the collection of blood.

BACKGROUND OF THE INVENTION

Self-sealing, gas-proof elastomeric closures or configurations are used extensively for sealing an open end of an air-evacuated blood collection tube. These types of closures not only provide an effective seal for maintaining a vacuum inside the collection tube, but are also penetrable by a cannula so that fluids may be deposited or withdrawn from the container without compromising the sterility of the inside of the container. While these types of closures have been utilized for a long time, improvements in their use and features are continually being made. For example, U.S. Pat. No. 4,111,326 explains many of the deficiencies of these prior closures, while offering improvements over these prior art closures, such as the use of less material for construction, reduction of manufacturing expense, easier assembly, and a much lower force needed to penetrate with a needle.

In addition to the many deficiencies of prior art closures, as pointed out in U.S. Pat. No. 4,111,326, other problems arise in the use of the air-evacuated blood collection tube. Specifically speaking, some blood collection tubes are inoperable due to the fact that something has caused the vacuum condition inside the blood collection container to dissipate. These collection tubes, sometimes referred to in the art as "dead tubes", are not only non-functional, but also are sometimes undetectable when "dead". In many instances, it is not until the user of the collection tube is attempting to collect blood that it is realized that there is no vacuum inside the container.

As a result, U.S. Pat. No. 4,293,078 provides a vacuum indicator closure for a blood collection tube. This device seals the open end of an air-evacuated blood collection tube and includes a tubular flexible elastomeric body having an open first end and a closed second end. The second end is formed by a cannula-penetrable, flexible elastic end wall having an outer surface and an inner surface. The outer surface of the end wall is convexly curved and the inner surface is concavely curved when pressure on both the inner and outer surfaces is equal. This end wall is sufficiently flexible to deflect under the influence of a pressure differential on the end wall so that when the pressure against the outer surface exceeds the pressure against the inner surface, the outer surface becomes concavely curved and the inner surface becomes convexly curved. This condition occurs when there is a vacuum inside the blood collection tube. The outer surface of the end wall is readily visible to an observer with its changeable nature serving as an indicator of relative pressures on the opposite sides of the end wall. A flange is annularly disposed around the periphery of the tubular body adjacent to the second end.

In usage, this device has been highly effective and is otherwise known as a "VACUTAINER" (TM) seal. Unfortunately, this closure is utilized only with standard glass blood collection tubes. Standard glass blood collection tubes have a variety of problems that make them unsuitable for the purposes contemplated by the makers of the closures for such tubes. As with any glass material, the glass blood collection tube is subject to a relatively easy breakage. Such breakage can destroy the sample collected within the tube and can cause other problems, i.e., injury, contamination of environment, exposure of individuals and environment to potential health hazards within the labs. Furthermore, this breakage potential is exacerbated by the fact that a great deal of pressure is required to join the closure to the open end of the blood collection tube at the time of manufacture. There have been a number of incidents in which the collection tube has broken upon the attempted removal of the closure from the tube. This presents an additional hazard to health care personnel.

Where glass collection tubes are utilized, shipment through the mail becomes quite difficult. In order to ship such extremely breakable material in the mail, a relatively complex shipping box must be developed. A great deal of cushioning-type material must be placed between each of the tubes in the potential shipment. In normal operations utilizing the standard postal services, boxes containing such tubes can be thrown about, compressed, or otherwise damaged. As a result, such blood collection tubes become broken and damaged during the shipment between the collection site and the lab. Furthermore, the labor requirements for assembling the shipping containers is a disadvantage to the use of such glass tubes. An ideal situation would be to simply enclose the blood collection tube in a box, or an envelope, seal the envelope, and send the collected blood to the lab.

With the spread of the AIDS virus, and other dangerous infectious diseases, it is extremely important that collected blood be maintained in a sealed environment. AIDS-contaminated blood can be a potential health hazard to those that would handle such glass collection tubes, especially lab personnel. Lab personnel are especially at high risk for exposure to contaminated blood because it requires a significant amount of pressure to remove the closure from the blood collection tube because of the manufacturing procedures (which require precise insertion and mating of the closure to the tube). Since removal must occur in the laboratory for analysis of the sample, injury can occur and does frequently.

As with most glass manufacturing operations, there are manufacturing difficulties in providing the tolerances required for the engagement of the closure of U.S. Pat. No. 4,293,078. Many times, the flow characteristics of glass cause dimensional differences between the closure and the open end of the glass tube. This may limit the ability to cause and to maintain a vacuum within the blood collection tube. In practice, those glass tubes that are manufactured in a relatively inaccurate and imprecise way must not be used. If they are not used, then the seal between the closure and the tube would be inadequate and would allow the loss of a vacuum.

It is known that glass is a less than adequate material for the containing of blood. Glass inherently contains many impurities. The trace elements and background materials within the glass of the tube can leach into the blood and be detected in the testing procedures. For example, there are many trace elements in the blood for which testing is carried out. However, when glass is used for the collection of the blood, the trace elements in the glass will diffuse into the blood and be of much higher levels than those trace elements that were in the original blood sample. The leaching of these trace elements into the blood can create many improper results in blood studies, cause misdiagnosis and mistreatment, or otherwise interfere with proper analytical techniques. As a result, the glass blood collection tubes can contribute to the inaccuracy of the blood studies.

Additionally, since glass is an extremely smooth material, there is not a great deal of friction between the surface of the closure and the inner surface of the blood collection tube. When the test tube has been manufactured with imprecise tolerances, the low amount of friction between the glass and the closure can allow the closure to slide outwardly from the open end of the glass tube and cause vacuum failure. In an effort to overcome this problem, the closure is made with an extremely long internal sleeve so as to engage the interior walls of the tube.

U.S. Pat. No. 4,856,533, issued on Aug. 15, 1989, to Anraku et al. describes a vacuum blood collection tube that is made of a polyethylene terephthalate material. Similarly, U.S. Pat. No. 4,735,832, issued on Apr. 5, 1988, to Ichikawa et al. describes a container made of a synthetic resin that could be used for containing blood. Both of these prior art patents describe the use of a liner material that is used for coating the interior of the tube. The purpose of this liner is to assist in the clotting of blood within the container. Since each of these prior art patents uses a liner material, this means that more material is used then is really needed to initiate the clotting action. Because of that, there may be some leaching of the material into the blood. The tubes of these prior art patents are injection blow molded. They are also lined with a less permeable plastic. As a result, the interface between the tube wall and the liner contributes to gas permeation.

During blood collection activities, it is usually desirable to have the blood clot within the tube. Silicon within the glass of a glass collection tube initiates this clotting function. When plastic is used as the tube, such as in these aforementioned prior art patents, silicon is not present and blood will have a tendency to not completely clot. Therefore, U.S. Pat. Nos. 4,856,533 and 4,735,832 utilize such lining materials to assist in this function. The use of a liner material, in addition to the problems stated hereinbefore, is difficult to apply, adds to the manufacturing expense, often does not effectively assist in the clotting of blood, and is more likely to be leached into the blood.

After experimentation, it was found that the closure of U.S. Pat. No. 4,293,078 was effective for maintaining vacuum in a glass blood collection tube. However, the tradeoff for the maintenance of this vacuum was that the closure of U.S. Pat. No. 4,293,078 makes it difficult to collect blood in an efficient ergonomic fashion. That is, the angle between the needle and the closure was such that it could not be used simply and easily by medical personnel for entering a vein. The extended interior sleeve of the closure and the extended exterior end of the closure requires that the needle be aligned away from the edges of the tube. As such, the closure of U.S. Pat. No. 4,293,078 presents an awkward angle for the collecting of blood from a vein. This makes it difficult, at times, for the needle to be slid a little way into the vein, as phlebotomists like to do. The needle may penetrate through the vein and into the back side of vein.

In order to collect blood, it is necessary to use an appropriate holder. These holders are typically identified as the "TERUMO VENOJECT" holders. This standard appliance receives the needle in a threaded opening at one end of the holder. This threaded opening is centered in an end surface at the end of the holder. The opening includes a double thread for the receipt of the needle. When the needle is attached, the blood collection tube is then placed within the holder so that one end of the needle will penetrate the closure. The vacuum of the closure will then cause blood to be sucked through the other end of the needle and into the collection tube.

The shape of the holder of the blood collection tube can cause additional problems. The small handles on the holder makes it difficult to turn the container so as to get a good angle. Also, the use of the double threaded opening means that the taper at the end of the needle can have a different angle to the vein depending on which of the "double threads" the needle body engages. In the collection of blood, for the safety and efficiency of the operation, it is desired that the longest end of the taper be at the lowermost position and that the needle be positioned nearly parallel to the vein.

It is an object of the present invention to provide an improved blood collection tube that has less breakage potential and stronger impact resistance.

It is another object of the present invention to provide a blood collection tube that simplifies procedures for the shipment of such tube.

It is a further object of the present invention to provide a blood collection tube that allows for manufacture with greater quality control, improved tolerances, greater efficiency, and less expensive procedures.

It is still a further object of the present invention to provide a blood collection tube that creates better fit between the open end of the tube and the closure.

It is another object of the present invention to provide an improved closure for a blood collection tube that allows the blood collection needle to assume a proper angle with respect to the vein.

It is another object of the present invention to provide an improved holder for a blood collection tube that causes the needle end taper to always assume the same position when used.

It is still a further object of the present invention to provide a blood collection system in which blood is collected in a safe, efficient, and consistent manner.

It is still another object of the present invention to provide a blood collection system that provides ease of use with decreased risk to the collector and patient.

These and other objects and advantages of the present invention will become apparent from a reading of the attached specification and appended claims.

SUMMARY OF THE INVENTION

The present invention is an improved blood collection tube comprising a tubular container of a polyethylene terephthalate material. The tubular container has an open end and a closed end. The open end has a flared exterior surface.

The open end of the tubular container has a hump that extends inwardly of the inner diameter of the open end and extends around the interior of the container.

The tubular container also has an edge at the open end. This edge is inclined so as to extend downwardly from the exterior to the interior of the tubular container. An indentation is provided on the inner surface on the side of the hump opposite the open end of the tubular container. The hump has a consistent shape around the inner diameter of the tubular container. The indentation is inclined and angled toward the inner diameter of the tubular container from the hump. The tubular container is comprised solely of a polyethylene terephthalate material.

The present invention is also an improved air-evacuated blood collection tube assembly that comprises an air-evacuated tubular container having an open end and a closed end and a cannula-penetrable self-sealing gas-proof closure in sealing engagement with the open end of the container so as to maintain the vacuum inside the container. The closure has one end interior of the container and the other end exterior of the container. The end interior of the closure has a first notch formed adjacent to the container wall. The closure has a first exterior notch that is formed in the end exterior. This exterior notch is aligned with the first notch on the end interior of the closure. The end interior also has a second notch formed adjacent the container wall and aligned with the first notch on the other side of the closure. The end exterior also has a second exterior notch on the other side of the closure aligned with the first exterior notch and aligned with the second notch on the end interior.

The closure has an indented ring formed about the first notch of the end interior for engaging the hump of the tubular container. The closure has a uniform surface formed between the first notch and the indented ring. This uniform surface is suitable for surface-to-surface sealing contact with the interior wall of the tubular container. The end exterior of the closure has a greater diameter than the end interior. The closure has a shoulder that is formed between the end exterior and the end interior. The shoulder is in sealing abutment with the open end of the tubular container.

The present invention is also a blood collection system that comprises a holder having a threaded needle-receiving opening on an end surface of the holder, a needle that is attached to this needle-receiving opening extending outwardly from the end surface, and an air-evacuated blood collection tube in fluid-tight engagement with the needle in a cavity of the holder. The blood collection tube collects blood as passed by the needle. The needle-receiving opening is offset from the center of the end surface so as to be generally aligned with the interior wall of the blood collection tube. The cavity of the holder is formed adjacent to the end surface so as to receive the blood collection tube.

The needle-receiving opening has a single threaded interior. The needle has an external single threaded portion. The single threaded interior of the needle-receiving opening and the exterior single threaded portion of the needle are configured such that bevelled portion of the needle end is always in the proper position whenever the needle is attached to the needle-receiving opening. The needle-receiving opening is in close proximity to the interior wall of the cavity of the holder. The end of the needle extends outwardly from the end surface of the holder When attached to the holder, the needle is positioned such that the end of the needle is aligned so as to be adjacent the periphery of the end surface. The short portion of the taper of the needle end is further removed from the end surface than the long portion The needle extends into the area of the first interior notch of the closure of the blood collection tube. The needle also extends into the area of the first exterior notch of the closure of the blood collection tube. By passing through these notched areas, the other end of the needle travels the route of least resistance through the closure so as to pass blood to the interior of the blood collection tube.

DETAILED DESCRIPTION OF THE DRAWINGS

FIG. 6 is a right side end view of the closure in accordance with the preferred embodiment of the present invention.

FIG. 7 is a view, in side elevation, of the closure of FIG. 4–6 as joined to the blood collection tube of FIGS. 1–3.

DETAILED DESCRIPTION OF THE INVENTION

Figure 1:
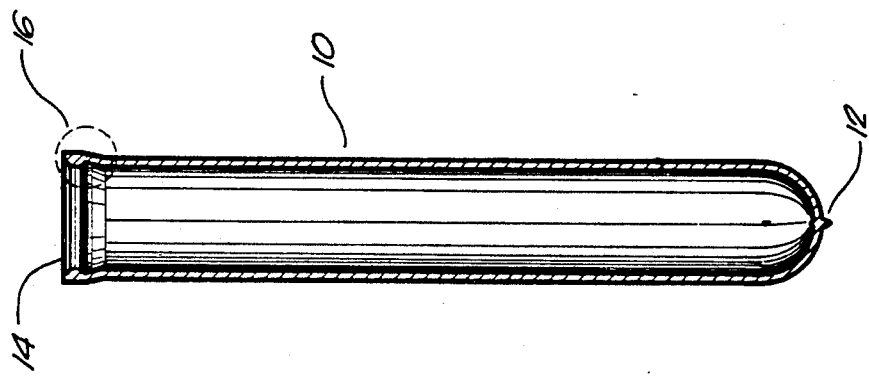
FIG. 1 is a cross-sectional view in side elevation of the blood collection tube of the present invention.

Referring to FIG. 1, there is shown at 10, the blood collection tube in accordance with the preferred embodiment of the present invention. The blood collection tube is elongate tubular cylinder having an enclosed end 12 and an open end 14 so that air can be evacuated from the tube 10 for its proper utilization. As will be described hereinafter, a closure member that is cannula-penetrable, self-sealing, and gas-proof will be positioned in sealing engagement in the open end 14 of blood collection tube so as to maintain a vacuum inside the tube 10.

In the present invention blood collection tube 10 is comprised of polyethylene terephthalate material. The polyethylene terephthalate is a fiber-forming polyester prepared from terephthalic acid or its esters and ethylene glycol. In the preferred embodiment of the present invention, the material of the tube 10 will be either KODAPAK PET Copolyester 9921 or KODAPAK PET 7352. These are condensation polymers produced from dimethyl terephthalate (DMT) and ethylene glycol using continuous melt phase polymerization process followed by a solid state polymerization process. The KODAPAK PET Copolyester 9921 is a clear material. The KODAPAK PET 7352 has a slight tint to it, but it is otherwise transparent. The material has strong resistance to weak acids at boiling temperature to strong acids in the cold, to weak alkalies, to bleaches, to most alcohols, ketones, soaps, detergents, and related agents. The material presents an extremely strong plastic that will not break even during extraordinary conditions of shipment and usage.

In FIG. 1, of particular note, is the circled area 16 which is a unique area formed on the present invention. The details of circled area 16 are shown in FIG. 3.

Figure 2:
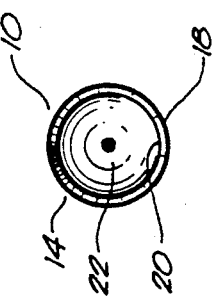
FIG. 2 is a top view of the blood collection tube of the present invention.

FIG. 2 is a top view taken across the open end 14 of blood collection tube 10. Specifically, blood collection tube 10 has a circular outer diameter 18 and a circular inner diameter 20. The blood is collected in the area bounded by the circular inner diameter 20 in space 22. Also, the closure, to be described hereinafter, will fit into the inner diameter 20 of blood collection tube 10.

Figure 3:
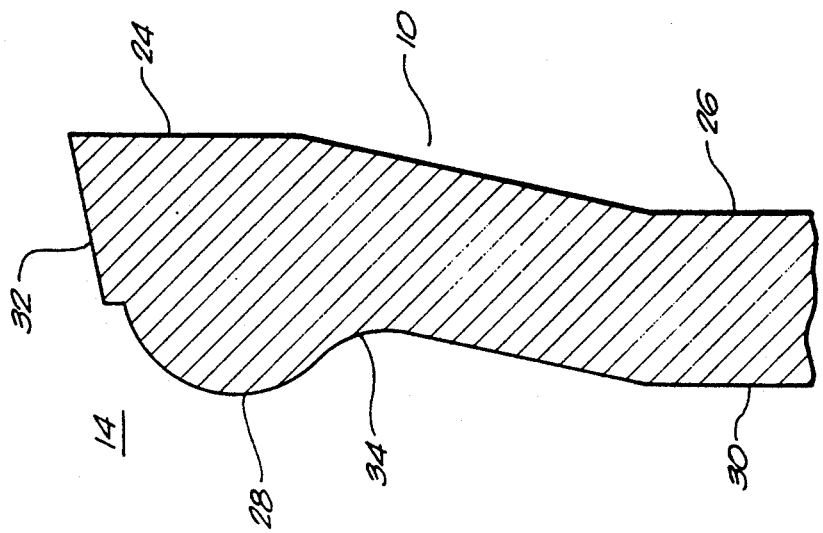
FIG. 3 is a detailed view showing the circled area of FIG. 1.

FIG. 3 illustrates the circled area 16 of FIG. 1. This is a unique aspect of the blood collection tube 10 of the present invention. Specifically, FIG. 3 shows the configuration of the blood collection tube 10 at the open end 14 of the tube. As can be seen, the open end 14 flares outwardly as represented by flared outer wall 24. In the process of molding the polyethylene terephthalate material in the injection molding process, it has been found that the use of a straight exterior wall 26 makes the blood collection tube 10 difficult to remove from the mold. In particular, there is nothing for a mechanical mechanism to grasp so as to remove the blood collection tube 10 from the mold. To facilitate the manufacturing of the blood collection tube 10, it was necessary to distort the open end 14 so as to create a flared outer wall 24 at this open end. By flaring the exterior wall 24 of blood collection tube 10, it was found that the manufacture of the blood collection tube could be greatly improved. The flaring of the open end 14 of the blood collection tube 10 is felt to be an important improvement for the purposes of manufacturing the tube of the present invention.

As can be seen in FIG. 3, at the open end 14 of the blood collection tube 10 is a hump 28 extending inwardly of the inner diameter 30 of the tube 10. This hump 28 is for the purpose of receiving the closure in a secure fashion. Hump 28 is of a consistent shape extending around the inner diameter 30 of the blood collection tube 10. The hump 28 is slightly removed from the top edge 32 of the open end 14 of tube 10. The upper edge 32 of tube 10 is inclined so as to extend downwardly from the flared exterior 24 to the interior 30 of the tube 10. This downward angle assists in the manufacture of the tube 10 and facilitates the insertion of the closure of the present invention. An indentation 34 is formed on the inner diameter 30 of tube 10 on the side of hump 28 opposite the edge 32. Indentation 34 serves to effect an affirmative surface-to-surface contact with the closure of the present invention. The indentation 34 has a gradual inward extending angle to the inner diameter 30 of the tubular container.

Figure 4:
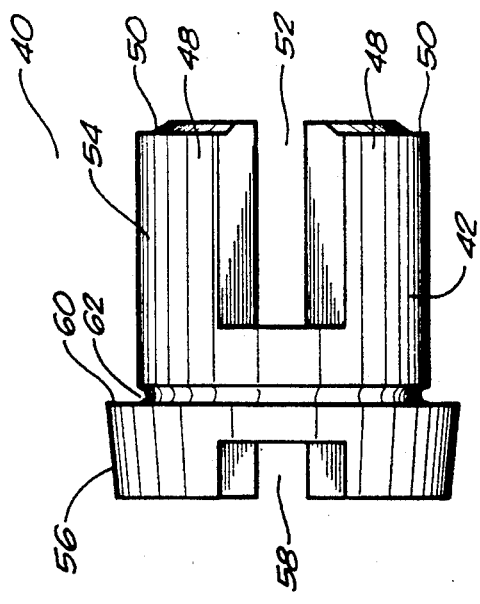
FIG. 4 is a view, in side elevation, of the closure in accordance with the preferred embodiment of the present invention.

FIG. 4 illustrates closure 40 of the present invention. Closure 40 is comprised of a tubular elastomeric body 42, preferably cylindrically shaped. Body 42 has flexible, elastic side walls 48, which are intended to snugly fit about their periphery in sealing engagement against the interior surface 30 of the blood collection tube 10. It should be noted that the lowermost portion of side walls 48 includes a smooth radius 50 to form the leading edge of the closure 40 and to facilitate its assembly into the blood collection tube 10.

In FIG. 4, body 42 includes a first notch 52 that extends through the side walls 48. Notch 52 has a generally rectangular shape and extends a considerable ways into the side walls 48. Tubular body 42 includes an end interior 54 and an end exterior 56. The end interior 54 is open on its interior. The closed end exterior 56 is formed by a cannula-penetrable flexible elastic wall that is integral with the side walls 48. It can be seen that the end exterior 56 includes a notch 58, of generally rectangular configuration, that is aligned with the notch 52 at the end interior 54 of the closure 40. A shoulder 60 is formed in the area between the end exterior 56 and the end interior 54. Shoulder 60 will be in abutment with the edge 32 of the open end 14 of blood collection tube 10. An indented ring 62 is formed adjacent to the shoulder 60 for receiving the hump 28 of the blood collection tube.

Figure 5:
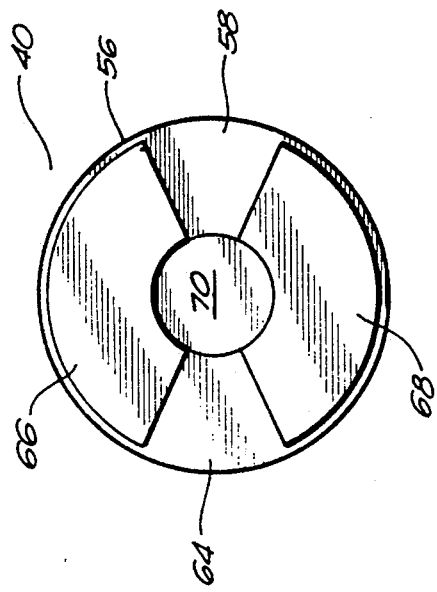
FIG. 5 is a left side end view of the closure of FIG. 4 in accordance with the preferred embodiment of the present invention.

Referring to FIG. 5, there is shown an end view of the end exterior 56 of the closure 40 of the present invention. Specifically, in FIG. 5, it can be seen that the end exterior 56 includes a first exterior notch 58 and a second exterior notch 64. It can be seen that these notches 58 and 64 extend between body sleeve portions 66 and 68. The first notch 58 is aligned with the second notch 64. Body sleeve portions 66 and 68 extend outwardly from the end surface of the notches 58 and 64. In FIG. 5, it can be seen that there is a central end wall 70 adjacent to the notches 58 and 64 of the closure 40. End wall 70 is a relatively thin, flexible diaphragm that spans the closure 40. During the formation of the closure 40, the end wall 70 is configured to have its outer surface convexly curved and its inner surface concavely curved when pressure on the inner and outer surfaces is substantially equal. If, for example, there is no vacuum inside the blood collection tube to which the closure 40 is attached, then the pressure on both sides of the end wall 70 will be in substantially atmospheric levels thereby establishing the shape of the end wall.

FIG. 6 shows the end interior 54 of closure 40. Specifically, it can be seen that the notch 52 is formed between the side walls 48. Side walls 48 will be in surface-to-surface contact with the interior walls of the blood collection tube. Also, another interior notch 72 is formed on the opposite side of side walls 48 from the first notch 52. The second notch 72 is aligned with the first notch 52 on the end interior 54 of the closure 40. Also, the notch 72 will be aligned with the second notch 64 of the second exterior notch 64 of the closure 40. Shoulder 60 extends outwardly from the side walls 48 so as to be in position for abutment to the edge 32 of the open end 14 of the blood collection tube 10.

FIG. 7 shows the configuration of the blood collection tube 10 with the closure 40 attached thereto. In FIG. 7, it can be seen that the end interior 54 is fitted within the interior wall 30 of the blood collection tube 10. The hump 28 (as shown in FIG. 3) will engage the indented ring 62 at the shoulder area 60 of the closure 40. The side walls 48 of the end interior 54 will be in sealed surface-to-surface contact with the indentation 34 and the side walls 30. Notch 52 of the end interior 54 is configured so as to be adjacent the interior wall 30 of tube 10. The area 74 of the closure 40 will create an affirmative gas-proof seal with the open end 14 of the blood collection tube 10.

The end exterior 56 of the closure 40 extends above the open end 14 and the edge 32 of the blood collection tube 10. Shoulder 60 is in abutment with this edge 32 of the open end 14 of blood collection tube 10. Notch 58 is positioned so as to be aligned with the interior notch 52. Notches 52 and 58 align so as to present a path of travel for the needle which would be inserted into the closure 40, to be described hereinafter.

It is the ability to mold the blood collection tube 10 from the polyethylene terephthalate material that allows the configuration of the closure 40 to be possible. When the blood collection tube was manufactured of glass, in prior art systems, it was necessary to have a large area of contact between the rubber closure 40 and the interior walls 30 of the blood collection tube. The greater the area of contact between the rubber and the glass, the greater security of seal that could be achieved. The length of the body portion 48 of the closure would be directly proportional to the reliability of the seal that could be established. Fortunately, the ability to manufacture the blood collection tube 10 of the present invention from the polyethylene terephthalate material allows for much greater tolerances to be achieved than in prior art glass manufacturing techniques. Therefore, the area of the body 48 of closure 40 can be greatly reduced. Additionally, the configuration of the open end 14 of the blood collection tube further enhances the creation of a positive seal between the closure 40 and the interior of the blood collection tube. As a result, it is possible to configure the closure 40 so as to have the notches 52 and 72 formed on the interior side. It is only the area that must be in sealing contact with the tube 10. This proper sealing can be established by the manufacture of the tube having the configuration shown in FIG. 3.

In use, the closure 40 has the thin flexible diaphragm 70 that is positioned between the end interior 54 and the end exterior 56. The purpose of this diaphragm is to present an affirmative indication of the user as to whether there is a vacuum within the blood collection tube 10. During the formation of the closure 40, the wall 70 is configured to have its outer surface convexly curved and its inner surface concavely curved when pressure on the inner and outer surfaces is substantially equal. If, for example, there is no vacuum inside the blood collection tube 10, then the pressure on both sides of the wall 70 will be in substantially atmospheric levels. This establishes the shape of the end wall 70. To the observer, the end wall 70, under these conditions, would appear to have a domed-shape protrusion. It is clearly discernible and readily apparent that there is no vacuum inside the blood collection tube 10. The dome appearance is readily visible to the observer as an indication of vacuum conditions in as much as the vacuum end 56 of the closure 40 lies beyond the open end 14 of the blood collection tube 10, preferably directly at the top of the entire blood collection tube assembly for clear visibility.

End wall 70 is a relatively thin diaphragm which is sufficiently flexible to deflect under the influence of a pressure differential across the wall 10. When vacuum conditions exist inside the blood collection tube 10, the pressure against the inside surface of the wall 70 is substantially less than the pressure against the outside surface of the wall 70, which, under normal condition, is generally at atmospheric pressure levels. With this kind of pressure differential against the end wall 70, the outer surface becomes concavely curved and the inner surface becomes convexly curved. Thus, the deflection of the end wall produces a clearly defined recess as seen by the observer. This observer will then be able to attribute such recess to the fact that a vacuum condition does exist inside the blood collection tube 10.

Figure 8:
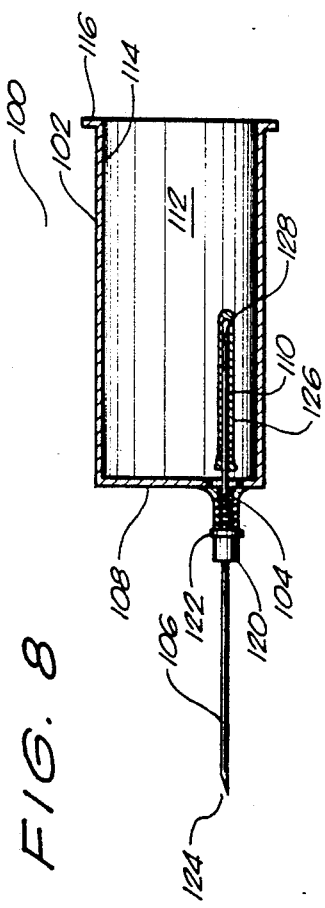
FIG. 8 is a cross-sectional view, in side elevation, of the holder and needle of the system of the present invention.

Referring to FIG. 8, there is shown at 100 the holder apparatus for the transmitting of blood into a blood collection tube. Apparatus 100 comprises a holder 102. Holder 102 has a threaded needle-receiving opening 104. A needle 106 is attached to the needle-receiving opening 104 so as to extend outwardly from the end surface 108 of the holder 102. Needle 106 has a portion 110 extending through the opening 104 and into the cavity 112 of the holder 102.

The holder 102 has a cylindrical body portion 114. One end 116 of the cylindrical body portion 114 of holder 102 is open for the purpose of receiving a blood collection tube. End 116 has a flanged portion that extends outwardly from the cylindrical body portion 114. The cylindrical body portion 114 defines the cavity 112. End surface 108 is connected to the body portion 114 opposite the end portion 116. The end surface 108 includes the needle-receiving opening 104. The needle-receiving opening 104 opens to the cavity 112 of holder 102. The needle-receiving opening 104 is offset from the center of end surface 108 and is generally closely positioned to the cylindrical wall 114 of holder 102.

The needle-receiving opening 104 is unique in that it has a single internal thread. The prior art systems have all had double threads.

Needle 106 includes a housing 120 that is attached to the exterior of needle 106. Housing 120 includes an abutment surface 122. Housing 120 also includes an externally threaded portion that is received by the internal threads of needle-receiving opening 104. The threaded portion of the needle 106 includes a single external thread. This matches the single internal thread of the needle-receiving opening 104. In this configuration, the advantage is that the needle will always be attached to the opening 104 in the same manner. When the abutment surface 122 encounters the end of the opening 104, then the ends of the needle will always be in their desired position.

As shown in FIG. 8, end 124 of needle 106 is tapered. The direction of this taper is such that the longest portion of the needle is adjacent to and aligned with the edge of the holder 102. The shortest end of the taper is closer to the central portion of the holder 102. In normal use, it is desirable that the longest portion of the taper be downward. When the end 124 enters a vein, it is desirable that the taper be in the direction shown in FIG. 8. The characteristics of the threads of opening 104 and of the housing 120 facility the positioning of this tapered portion.

Needle 106 extends into the cavity 112 of holder 102. A flexible sheath 126 extends around the other end of needle 106. Sheath 126 is for the purpose of preventing accidental stabs and of preserving the sterility of the needle during the attachment process. The other pointed end 128 of needle 106 is used for the purpose of penetrating the closure and entering the blood collection tube.

The configuration of FIG. 8 is a superior configuration over prior holders for blood collection tubes. As can be seen, the blood collection tube holder 100 of FIG. 8 has a needle that is adjacent to one of the walls 114 of holder 102. As such, the needle 106 presents a lower angle more favorable for a vein puncture. When inserting the needle into the patient, it is desirable that the end 124 of needle 106 have the taper shown in FIG. 8 and be inserted in the direction of the needle. In contrast to prior art systems, the present invention is more likely to enter the vein cleanly and avoid the perforating of the vein because of the guaranteed alignment of bevel of needle and holder.

Figure 9:
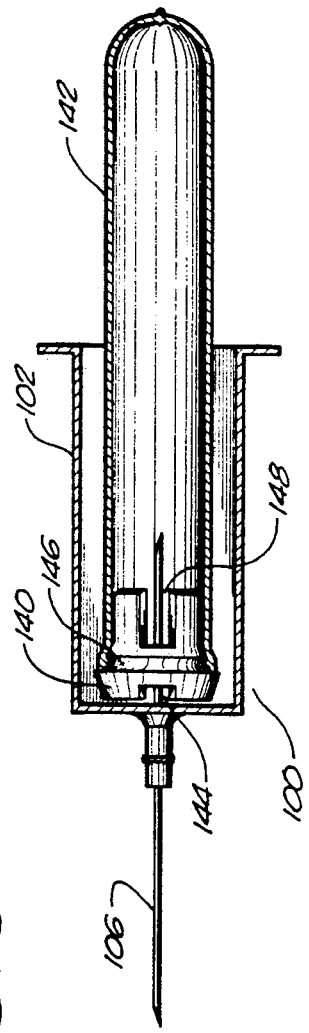
FIG. 9 is an illustration showing the configuration of the blood collection tube as positioned within the holder of the present invention.

FIG. 9 is a bottom view of the holder system 100 of the present invention. Specifically, in FIG. 9 it can be seen that the needle 106 extends through the closure 140 of the blood collection tube 142. Closure 140 has a configuration similar to the closure shown in FIGS. 4–6. It can be seen that the needle 106 is inserted into the area of closure 140 past the notch 144. The needle 106 penetrates the thin diaphragm seal, passes through the sealing portion 146 of closure 140, and passes outward through the notch 148 of the end interior of the blood collection tube 142. With reference to FIG. 8, the needle is in close proximity to the outer edge of the holder 102. Similarly, the needle 106 is in generally close proximity to the interior wall of blood collection tube 142. The notching of the closure 140 allows the needle 106 to travel the path of least resistance. Also, the notches provide a visual indication to the user of the proper alignment of the blood collection tube within the holder. In addition, the needle can travel this path of least resistance while maintaining the proper profile as shown in FIG. 8. As such, the present invention offers a superior system for the entry into the vein of a patient and a superior system for the withdrawal of blood from the patient.

Figure 10:
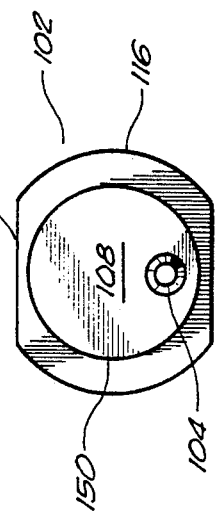
FIG. 10 is an end view showing the holder in accordance with the system of the present invention.

FIG. 10 is an end view showing the holder 102. Specifically, in FIG. 10, holder 102 includes the needle-receiving opening 104. It can be seen that the needle-receiving opening 104 is offset from the center of the end surface 108. As such, it presents a low profile generally adjacent to the wall 150 of the holder 102. The back surface 116 extends outwardly beyond the wall 150 of the holder 102. The flat edges 152 at the top and the bottom of the holder 102 for the purpose of supporting the holder on a flat surface and to prevent rolling from occurring. As stated previously, the needle-receiving opening 104 keeps the needle at a low profile relative to the body of the holder 102. As such, the needle will more easily penetrate the vein and be in a better position for collecting blood. The needle will be as parallel as possible to the vein during blood collection.

Figure 11:
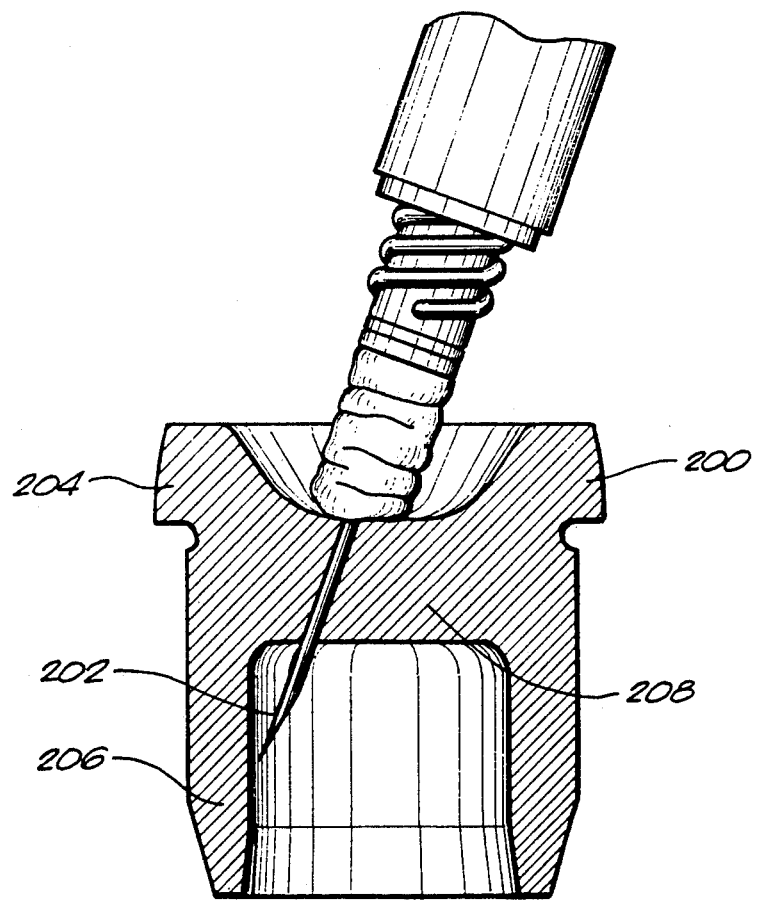
FIG. 11 is an illustration of the prior art technique for filling the blood collection tube.

FIG. 11 shows the prior conventional technique for the collection of blood with the blood collection tube. FIG. 11 has no bearing on the description of the present invention. FIG. 11 is simply for the illustration of the prior art techniques. In FIG. 11, the needle is positioned at a sharp angle relative to the direction of the blood collection tube 200. Specifically, needle 202 is inserted through the wall of the closure 204. Since it is difficult to penetrate the body portion 206, the needle 202 must be inserted through the narrow diaphragm area 208. In this position, the other end of the needle must be tilted at a great angle relative to the blood collection tube 200. As such, when inserting the needle into a vein, the blood collection tube is positioned in an awkward position generally transverse to the vein. It is a goal during the collection of blood to maintain the needle in as parallel of a position as possible to the direction of the vein. This goal is difficult to meet with configuration of the prior art systems for the collection of blood in blood collection tubes.

A large number of advantages result from the combination of the blood collection tube of polyethylene terephthalate material and the closure. Initially, it can be seen from the enclosed drawings that there is close tolerance between the open end of the blood collection tube and the closure. During the hand assembly of the closure with the blood collection tube, the blood collection tube will never break, shatter, or otherwise present hazards to the person assembling the closure with the tube. Since polyethylene terephthalate is extremely strong and crack-resistant, the health care worker assembling the closure with the tube will have little to fear.

The blood collection tube of the present invention is also extremely resistant to any sort of damage during standard postal procedures. These tubes of polyethylene terephthalate can bang together, jar, and withstand great pressures placed upon them. As a result, little care is required in assembling the mailing package containing the blood collection tubes of the present invention. After testing, the blood collection tube of the present invention will withstand any compressive forces generating during standard postal procedures.

The process of molding the blood collection tube of the present invention is a relatively simple procedure, as compared to the processes for manufacturing glass tubes. Even though this is a relatively simple procedure, great manufacturing tolerances can be achieved. Manufacturing tolerances are important when considering the nature of the relationship between the closure and the open end of the tube. As such, the tube of the present invention will be accommodate the closure in an extremely uniform and tight fashion.

The use of polyethylene terephthalate material is superior to the use of glass. Importantly, the polyethylene terephthalate is free of background materials. There should be no dispersion of any background and trace elements into the blood contained within the tube. As such, the present invention should contribute to the accuracy and precision of blood studies.

In contrast with the prior art patents, the polyethylene terephthalate tubes are injection molded and not blow-molded. As a result, the tubes of the present invention are thicker and are less gas permeable and will hold a vacuum for a period of time. There is no need for a lining to improve the gas permeation. Therefore, there is no leaching of material into the blood or leaching of certain elements out of the blood into the material. Small glass beads may be used with a surface area corresponding to the amount of blood in the tube. This will provide enough silicon exposure to the blood to allow for the initiation of clotting. Once the clotting starts, the glass surface will be so small that it will be insignificant to the level of silicon that may already be in the blood. As soon as the blood is spinned down, the glass beads will travel through the serum separator and be separated from the serum. As a result, all leaching of any non-blood material will be accomplished.

In contrast with other plastics, the use of polyethylene terephthalate is the most appropriate for blood collection tubes. Polyethylene terephthalate will not breathe. As such, the material used for the blood collection tube will maintain the vacuum for a very long period of time. Experiments have shown that a vacuum can be maintained for over 200 days. The use of the polyethylene terephthalate for the blood collection tube is superior to glass or other plastic materials.

An additional benefit of the present invention is the texture of the polyethylene terephthalate blood collection tube. The texture of the inner surface of the blood collection tube allows for greater frictional engagement between the closure and the blood collection tube, as opposed to prior art glass tubes. As a result, it becomes difficult to remove the closure after it is assembled onto the tube. This engagement is further enhanced by the configuration of the very top edge of the blood collection tube. The use of the inclinations, angles, and humps, enhances the ability to engage the closure in a gas-proof manner. No accidental dislodgment should occur during normal usage and during shipment through standard postal procedures.

It should be noted that the polyethylene terephthalate plastic material is much more recyclable than other types of plastic. As a result, for its use as a blood collection tube, the tube of polyethylene terephthalate material is much more friendly to the environment and serves to enhance environmental quality. The polyethylene terephthalate material for the blood collection tube of the present invention is easy to work with, can be easily disposed of, and can be incinerated as easily as glass.

As a result of the benefits of the present invention, the present invention offers a significant improvement over the prior art blood collection tube assemblies. The present invention reduces the spread of blood-borne diseases by reducing the possibility of leakage during shipment of the blood. The present invention also reduces hazards to health care personnel utilizing such blood collection enclosures. The unique closure of the present invention allows for the proper collection of blood by maintaining the needle at a position virtually parallel to the vein from which the blood is collected.

The physical embodiments illustrated and discussed in the specification is intended only to teach those skilled in the art the best way known by the inventor to make and use the invention. Nothing in the specification should be considered as limiting the scope of the present invention. Any changes could be made by those skilled in the art to produce equivalent systems without departing from the invention. The present invention should only be limited by the following claims and their legal equivalents.

I claim:

1. An air-evactuated blood collection tube assembly comprising:
    an air-evactuated tubular container having an open end and a closed end, said tubular container formed of a polyethylene terephthalate material, said open end flared outwardly, said open end of said tubular container having a hump extending inwardly of an inner diameter of said tubular container; and
    a cannula-penetrable self-sealing gas-proof closure in sealing engagement in the open end of said container so as to maintain a vacuum inside said container, said closure having one end interior of said container and another end exterior of said container, said end interior having a surface in continuous sealing contact with said container, said end interior having an annular sleeve extending from said surface toward said closed end, said annular sleeve having a first notch extending through a wall of said annular sleeve and juxtaposed against said container, said closure having an indented ring formed about said first notch of said end interior and said indented ring engaging said hump of said tubular container.

2. The assembly of claim 1, said closure having a first exterior notch formed in said end exterior, said first exterior notch aligned with said first notch on said end interior of said closure.

3. The assembly of claim 2, said end interior having a second notch formed through a wall of said annular sleeve juxtaposed against said container on another side of said closure.

4. The assembly of claim 3, said end exterior having a second exterior notch formed on an opposite side of said closure from said first exterior notch, said second exterior notch aligned with said second notch on said end interior.

5. The assembly of claim 1, said end exterior of said closure having a greater diameter than said end interior, said closure having a shoulder formed between said end exterior and said end interior, said shoulder in abutment with said open end of said tubular container.

6. An improved blood collection tube, the improvement comprising:
    a tubular container having a body of a polyethylene terephthalate material, said tubular container having an open end and a closed end, said tubular container having a flared area of gradually increasing diameter adjacent said open end, said body and said flared area defining generally constant wall thickness, said flared area having an outer diameter greater than said body, said open end of said tubular container having a hump extending inwardly of an inner diameter adjacent said open end.

7. The improvement of claim 6, said tubular container having an angled edge at said open end, said angled edge inclined so as to extend downwardly from the exterior to the interior of said tubular container.

8. The improvement of claim 6, said tubular container having an indentation on the inner diameter on the side of said hump opposite said open end.

9. The improvement of claim 8, said hump being of consistent shape around the inner diameter of said tubular container, said indentation inwardly angled toward the inner diameter of said tubular container.

10. The improvement of claim 6, said tubular container comprised solely of a polyethylene terephthalate material.

* * * * *